United States Patent
Schertiger et al.

(10) Patent No.: US 10,350,381 B2
(45) Date of Patent: Jul. 16, 2019

(54) CLOSING OF FLOW THROUGH CATHETER

(71) Applicant: Coloplast A/S, Humlebaek (DK)

(72) Inventors: Lars Olav Schertiger, Fredensborg (DK); Helle Haraldsted, Glostrup (DK)

(73) Assignee: Coloplast A/S, Humlebaek (DK)

( * ) Notice: Subject to any disclaimer, the term of this patent is extended or adjusted under 35 U.S.C. 154(b) by 541 days.

(21) Appl. No.: 15/016,983

(22) Filed: Feb. 5, 2016

(65) Prior Publication Data

US 2016/0151604 A1 Jun. 2, 2016

Related U.S. Application Data

(62) Division of application No. 14/241,890, filed as application No. PCT/DK2012/050313 on Aug. 28, 2012.

(30) Foreign Application Priority Data

Aug. 29, 2011 (DK) .............................. 2011 70472
Aug. 28, 2012 (WO) ................ PCT/DK/2012/05031

(51) Int. Cl.
*A61M 25/00* (2006.01)
*A61M 25/10* (2013.01)
*A61M 25/01* (2006.01)

(52) U.S. Cl.
CPC ...... *A61M 25/002* (2013.01); *A61M 25/0017* (2013.01); *A61M 25/0045* (2013.01); *A61M 25/10* (2013.01); *A61M 2025/0004* (2013.01); *A61M 2025/0018* (2013.01); *A61M 2025/0175* (2013.01); *A61M 2202/0014* (2013.01); *A61M 2202/0496* (2013.01)

(58) Field of Classification Search
CPC ........ A61M 25/002; A61M 2025/0006; A61M 2025/0024; A61M 25/0074; A61M 25/0017; A61M 2025/0018; A61M 2025/0175; A61M 2202/0014; F16B 7/1463
USPC ........................................ 206/210; 604/544
See application file for complete search history.

(56) References Cited

U.S. PATENT DOCUMENTS

| | | | |
|---|---|---|---|
| 1,120,549 | A | 12/1914 | Schellberg |
| 3,332,424 | A | 7/1967 | Minteer |
| 3,606,889 | A | 9/1971 | Arblaster |
| 3,642,004 | A | 2/1972 | Osthagen et al. |
| 3,782,381 | A | 1/1974 | Winnie |
| 3,898,933 | A | 8/1975 | Castera et al. |
| 3,967,728 | A | 7/1976 | Gordon et al. |
| 4,230,115 | A | 10/1980 | Walz, Jr. et al. |
| 4,361,148 | A | 11/1982 | Shackleford et al. |
| 4,500,313 | A | 2/1985 | Young |

(Continued)

FOREIGN PATENT DOCUMENTS

| | | |
|---|---|---|
| GB | 2032556 A | 5/1980 |
| RU | 2294154 C2 | 2/2007 |

(Continued)

*Primary Examiner* — Robert Poon
(74) *Attorney, Agent, or Firm* — Coloplast Corp., Coloplast A/S; Nick Baumann

(57) ABSTRACT

An assembly comprising a catheter package, a catheter and a collecting bag is provided. The assembly has means for preventing flow of liquid through the catheter during storage. A sealing element closing the eyelets is provided. An extended cone-lock in a telescopic catheter is also provided.

22 Claims, 3 Drawing Sheets

(56) References Cited

U.S. PATENT DOCUMENTS

| | | |
|---|---|---|
| 4,601,713 A | 7/1986 | Fuqua |
| 4,622,033 A | 11/1986 | Taniguchi |
| 4,871,358 A | 10/1989 | Gold |
| 5,183,470 A | 2/1993 | Wettermann |
| 5,290,229 A | 3/1994 | Paskar |
| 5,591,132 A | 1/1997 | Carrie |
| 5,681,274 A | 10/1997 | Perkins et al. |
| 6,010,479 A | 1/2000 | Dimitri |
| 6,358,229 B1 | 3/2002 | Tihon |
| 6,610,005 B1 | 8/2003 | Tao |
| 2003/0060807 A1* | 3/2003 | Tanghoj ............. A61M 25/0017 604/544 |
| 2004/0158231 A1* | 8/2004 | Tanghoj ................... A61F 5/44 604/544 |
| 2005/0085842 A1* | 4/2005 | Eversull ................. A61F 2/966 606/191 |
| 2006/0163097 A1* | 7/2006 | Murray ............. A61M 25/0009 206/364 |
| 2007/0088330 A1 | 4/2007 | House |
| 2009/0314676 A1 | 12/2009 | Peck et al. |
| 2010/0211049 A1 | 8/2010 | Schertiger et al. |
| 2010/0211050 A1* | 8/2010 | Luther ............. A61M 25/0017 604/544 |
| 2011/0077591 A1 | 3/2011 | Plicchi et al. |
| 2011/0224653 A1* | 9/2011 | Torstensen ........ A61M 25/0017 604/544 |
| 2012/0110951 A1* | 5/2012 | van Groningen ... A61M 25/002 53/425 |
| 2012/0168324 A1* | 7/2012 | Carleo ............. A61M 25/0014 206/210 |
| 2014/0262860 A1* | 9/2014 | Hagel ................. A61M 25/002 206/210 |

FOREIGN PATENT DOCUMENTS

| | | |
|---|---|---|
| WO | 97/41811 A1 | 11/1997 |
| WO | 2005073091 A2 | 8/2005 |
| WO | 2006/092150 A1 | 9/2006 |
| WO | 08138351 A1 | 11/2008 |
| WO | 08138352 A1 | 11/2008 |
| WO | 2009150487 A1 | 12/2009 |
| WO | 2011/011023 A1 | 1/2011 |
| WO | 11063816 A1 | 6/2011 |

* cited by examiner

CLOSING OF FLOW THROUGH CATHETER

CROSS-REFERENCE TO RELATED APPLICATIONS

This application is a divisional of U.S. application Ser. No. 14/241,890, filed Feb. 28, 2014, which claims the benefit under 35 U.S.C. § 371 National Stage to International Application No. PCT/DK2012/050313, filed Aug. 28, 2012, which claims the benefit of priority to Denmark Application No. PA 2011 70472, filed Aug. 29, 2011, which are hereby incorporated by reference in their entirety.

The invention relates to an assembly comprising a catheter stored in a package and a urine collecting bag. The catheter is stored in a liquid swelling medium in the package. The catheter or package comprises means for closing the flow through the catheter prior to use.

BACKGROUND

Catheter packages exist in which a hydrophilic coated catheter is stored in liquid swelling medium. When such a catheter package is combined with a urine collecting bag into a catheter kit, it is undesirable that the liquid swelling medium enters the bag. This makes it uncertain how large an amount of liquid is present in the container or package for wetting the catheter. If there is not enough swelling medium present then the catheter may dry out. Furthermore, many types of swelling medium evaporate into a crystalline structure which may clog the construction, thereby preventing liquid from flowing through the catheter and into the urine collecting bag when the catheter is to be used. Finally, swelling medium in the urine collecting bag is perceived unhygienic, and for a user where hygiene is important such perception may deter him from using the product.

Thus, there exists a need for an assembly as described where it is prevented that liquid flows from the catheter and into the urine collecting bag before use of the catheter assembly.

DESCRIPTION OF RELATED ART

International publication no. WO2011011023 discloses a catheter assembly including a tubular member having a first end and a second end. A catheter has a first end and a second end. At least a portion of the catheter is disposed within the tubular member. The first end of the tubular member is openable by axial movement of the catheter. A sealing engagement is provided between the tubular member and the catheter.

SUMMARY OF THE INVENTION

The invention relates to an assembly with a package for a catheter, a catheter stored in a cavity and a urine collecting bag communicating with the catheter. The catheter is a hydrophilic coated catheter stored in liquid swelling medium. During storage, the liquid swelling medium should be prevented from travelling from the cavity through the catheter and into the collecting bag. Thus, this invention provides means for preventing flow of liquid through the catheter during storage.

DETAILED DESCRIPTION OF THE INVENTION

In a first aspect, the invention relates to an assembly comprising a catheter package, a hydrophilic coated catheter and a urine collecting bag, the collecting bag being attached to or communicating with the catheter so that, in use, urine is able to flow through the catheter and into the collecting bag, the assembly comprising
- a cavity in the package adapted for storing the hydrophilic coated catheter and liquid swelling medium for wetting the coating on the catheter; and
- a liquid stop in the cavity or catheter so that the liquid swelling medium is prevented from flowing from the cavity, through the catheter and into the urine collecting bag during storage.

By providing an assembly with a liquid stop in the cavity or catheter, liquid is prevented from flowing through the catheter during storage. This has the effect that the liquid swelling medium is prevented from escaping from the cavity and furthermore prevented from soiling the urine collecting bag prior to use. Thus, the drawbacks mentioned above are eliminated.

In the following, whenever referring to the proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction from the distal to the proximal end. The transverse direction is the direction perpendicular to the longitudinal direction, which corresponds to the direction across the shaft of the catheter.

The catheter described in this application may be used as an intermittent urinary catheter.

The catheter comprises a main tubular part extending from the distal end to the proximal end. The tip is positioned in the proximal end of the catheter and is provided as a rounded closed end of the tube constituting the main part of the catheter. The connector is provided in the distal end and may in an embodiment comprise a flared end of the catheter so that the diameter of the connector increases with respect to the tubular part.

Usually catheters used as urinary draining devices are from size 8 FR to size 18 FR. FR (or French size or Charriere (Ch)) is a standard gauge for catheters, approximately corresponding to the outer circumference in mm. More accurately, the outer diameter of the catheter in mm corresponds to FR divided by 3. Thus, 8 FR corresponds to a catheter with an outer diameter of 2.7 mm and 18 FR corresponds to a catheter with an outer diameter of 6 mm.

The catheters of this invention are prior to use provided with a hydrophilic coating so as to impart a low-friction insertion.

The invention provides a liquid stop in the cavity or the catheter. This liquid stop functions as means for preventing flow through the catheter during storage. The liquid stop is adapted either to prevent flow of liquid into the catheter, when the catheter is stored, or to prevent flow of liquid through the catheter during storage. In the latter case liquid is prevented from travelling from the proximal end of the catheter and out through the distal end. However, when the catheter is to be used and is removed from the package then urine should be able to flow through the catheter from the proximal end to the distal end and from there into the urine collecting bag. Thus, when the catheter is to be used, the liquid stop is inactivated. In other words, the liquid stop is only able to prevent liquid flow during storage and will allow liquid flow when the catheter is to be used.

The assembly can be in storage position and in use position. In storage position the catheter is packed inside the cavity of the package and liquid flow from the cavity to the urine collecting bag through the catheter is prevented due to the liquid stop. In use position, the catheter is removed from the cavity of the package and liquid is able to flow from the proximal end of the catheter, through the catheter and out through the distal end of the catheter into the urine collecting bag.

The assembly of the invention comprises a urine collecting bag communicating with the catheter. In the simplest form, the collecting bag may be welded or glued directly onto the catheter. However, the urine collecting bag may also be attached through a connecting piece.

The urine collecting bag may be made of foil material, for example Polyethylene, and may be able to contain a volume of up to approximately 750 ml.

The liquid stop may comprise a closure preventing urine flowing into the catheter through the eyelets, when the catheter is stored.

In one embodiment of the invention, the cavity of the package is provided with a sealing element, which is adapted for sealing the eyelets to the catheter.

A closure or a sealing element at the eyelets is a simple solution that is easy to incorporate. It also has the effect that liquid swelling medium is completely prevented from entering into the catheter, thus the risk of crystalisation of the liquid swelling medium inside of the catheter is alleviated.

The sealing element may be in form of an element of closed cell foam (e.g. PU-foam) provided with a hole for inserting the proximal end of the catheter with the eyelets. The dimension of the sealing element in the longitudinal direction should be larger than the distance from the extreme proximal tip of the catheter to the most distal part of eyelets. This ensures that the sealing element covers the eyelets completely and thereby prevents liquid swelling medium from entering through the eyelets into the catheter.

A very soft polymeric material may also be used for the sealing element.

In one embodiment of the invention, the catheter is a telescopic catheter comprising an outer catheter part and an inner catheter part, which are provided with a cone-lock between the two parts. The cone-lock may be as described in the section: "Detailed Description of the Drawing". In this embodiment, the sealing is provided as an extension of the cone-element, which may cooperate with a sealing element on an inner surface of a distal end of the outer catheter part to prevent liquid flow through the catheter. Alternatively, the extension may be provided with a sealing element adapted for sealing on an inner surface of a distal end of the outer catheter part to prevent liquid flow through the catheter.

The distal end of the outer catheter part may be provided with a handle. In this case, the sealing element may be provided at an inner surface of the handle. Alternatively or additionally the handle may be provided with a reduced inner diameter with respect to the inner diameter of the outer catheter. This allows for a secure sealing while still allowing unimpeded movement of the inner catheter with respect to the outer catheter part.

In this embodiment, the inner catheter part as well as the outer catheter part is adapted for insertion into the urethra. This means that both catheter parts have dimensions within the regular French sizes—that is between 8 FR and 18 FR. Furthermore, both catheter parts are provided with hydrophilic coating.

The sealing ring may be made of TPE for example Santoprene®.

The outer diameter of the extended conus lock should be smaller than the inner diameter of the outer part of the catheter. Otherwise, the extension will prevent movement of the outer catheter part with respect to the inner catheter part.

In an embodiment of the invention, the extension of the cone-lock may be provided with outlet for the urine.

DETAILED DESCRIPTION OF THE DRAWING

Figure 1:
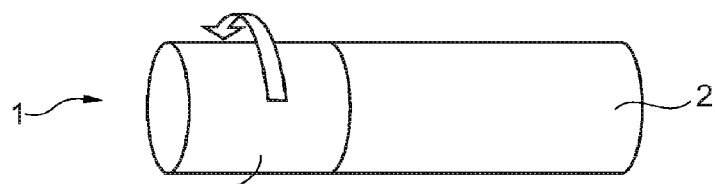
FIGS. 1-4 illustrate an assembly according to the invention

FIGS. 1-4 show in a stepwise sequence a catheter assembly 1 and how the catheter is prepared for use. The different embodiments disclosed herein may be incorporated into the catheter assembly 1 by a person skilled in the art. FIG. 1 shows the assembly in the storage position.

Figure 2:
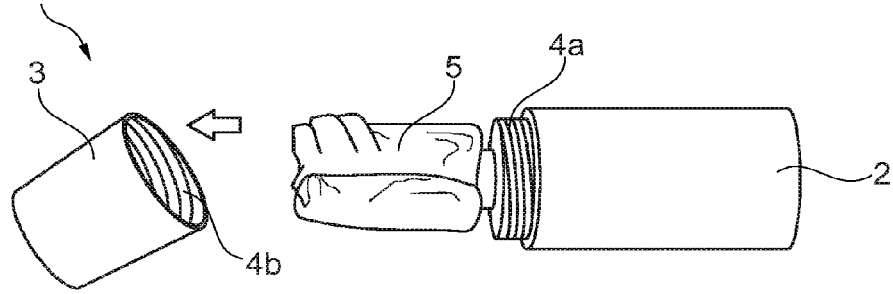

The catheter assembly comprises a container 2 and a cover 3 for closing off and covering an opening of the container 2. The container 2 defines the cavity 2a for storing the catheter. The cover 3 is removed by twisting the cover 3 around along the arrow as shown in FIG. 1. This releases the cover 3 from the threaded coupling 4a, 4b as shown in FIG. 2, which exposes a urine collecting bag 5 which has been folded inside the cover 3. The cover 3 may be discarded or saved for later re-closing of the catheter assembly 1.

Figure 3:
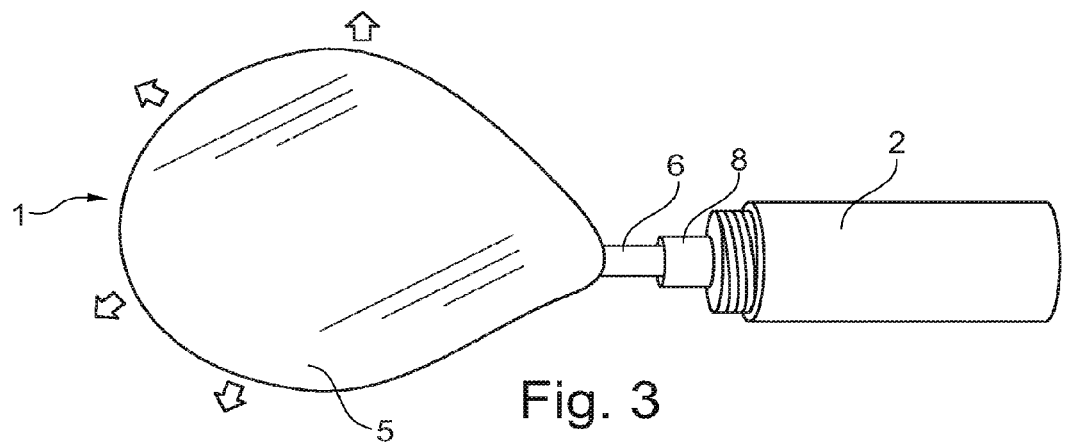

The urine collecting bag 5 is unfolded exposing a catheter handle 6 around which it was folded as seen in FIG. 3. The handle 6 is attached to the distal end 7 of a catheter 8. The handle is coupled with a neck portion 9 of the container, which defines an opening of the container 2 through which the catheter 8 can be inserted and retrieved.

Figure 4:
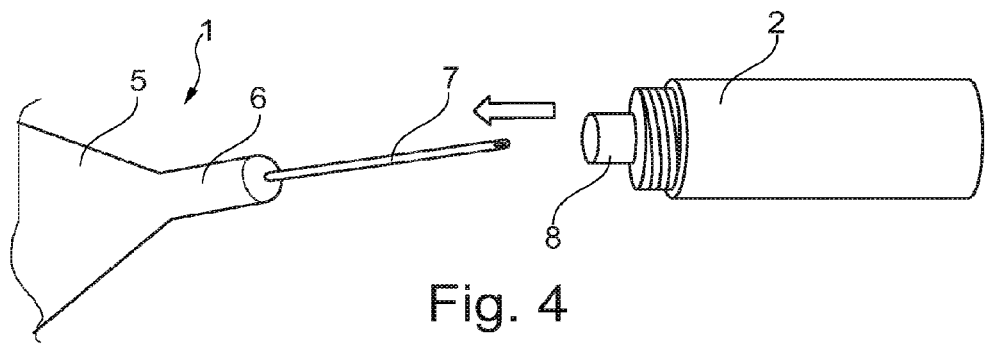

Finally, the catheter 8 and the urine collecting bag 5 are removed from the container 2 by pulling the handle 6 as shown in FIG. 4, whereby the catheter 8 is ready for insertion into the urethra. Thus, FIG. 4 shows the assembly in the use position.

The catheter is hydrophilic coated and stored together with a swelling medium (FIG. 5) in the container 2.

Figure 5:
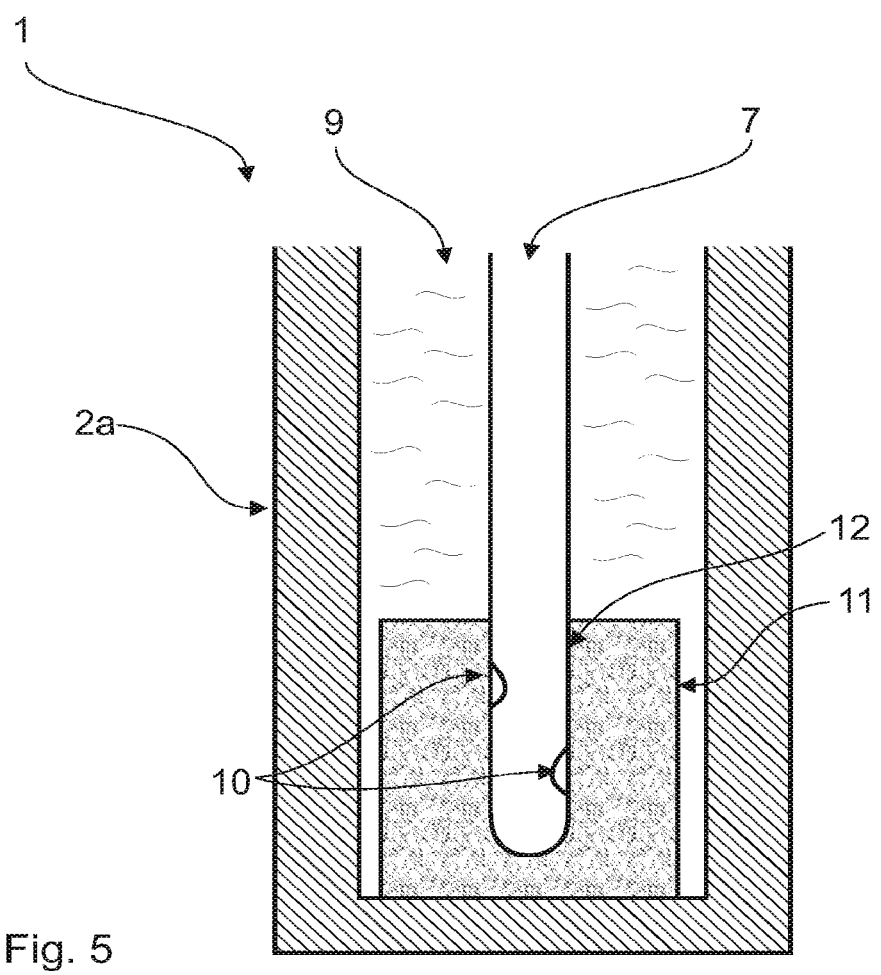
FIG. 5 illustrates a closure of the eyelets by a foam element

FIG. 5 illustrates a cross-section of a part of the catheter assembly 1 shown in FIG. 1 to FIG. 4. The assembly 1 has a cavity 2a including a catheter 8 and the liquid swelling medium 9. The catheter is provided with eyelets 10, which in use leads the urine from the bladder and through the catheter. A sealing element 11 is inserted in the cavity 2a, so that liquid swelling medium 9 contained in the cavity 2a is prevented from entering into the catheter 7, through the eyelets 10. The sealing element 11 may be made of closed cell foam or a soft polymeric material. The sealing element 11 is provided with a hole 12 adapted in size to the outer dimension of the catheter.

Figures 6, 7:
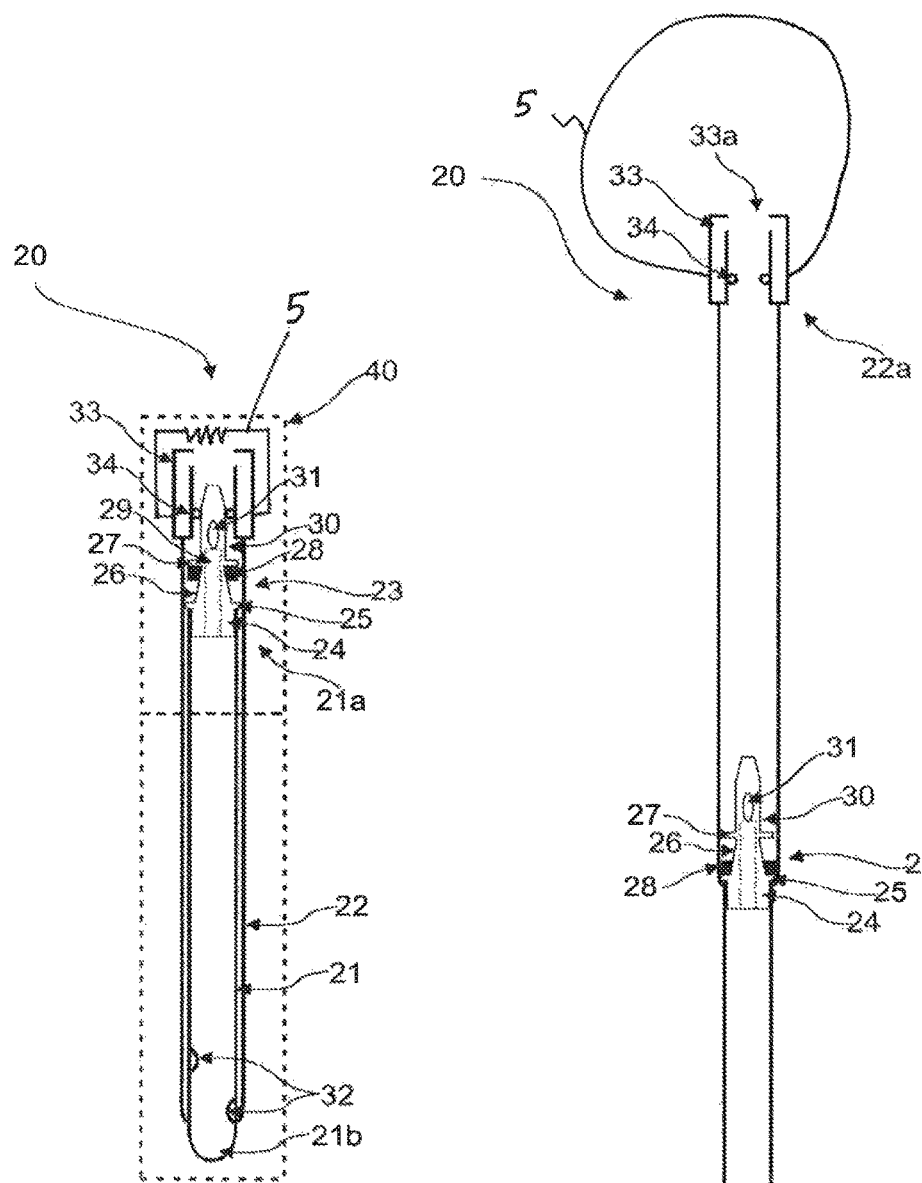
FIG. 6 illustrates a telescopic catheter with an extended cone-lock in the storage configuration i.e. when the assembly is in the storage position
FIG. 7 illustrates a telescopic catheter with an extended cone-lock in the extended (ready-to-use) configuration i.e. when the assembly is in the use position.

FIGS. 6 and 7 illustrate a telescopic catheter 20. In FIG. 6, the catheter is shown in the collapsed configuration (the stored configuration) and in FIG. 7 the catheter is shown in the extended configuration, when the catheter is ready to be used.

The catheter comprises an inner catheter part 21 and an outer catheter part 22 that are connected through a cone-lock 23. The cone-lock is attached to the distal end 21a of the inner catheter part by an attachment 24 extending into the catheter part. A first stop 25 is provided at the distal end 21a of the inner catheter part. Distally of this first stop, the cone-lock comprises a cone-element 26 followed by a second stop 27. Between the two stops, a locking element 28 is provided. This locking element engages frictionally with the inner surface of the outer catheter part, when the locking element 28 is positioned at the first stop 25. At the second stop 26, the locking element 28 is not engaged with the inner surface of the outer catheter part, thus when the element 28 is at this position, the inner catheter part 21 can move with respect to the outer catheter part 22. These parts, the two stops 25, 27, the cone-element 26, the attachment part 24 and the locking element 28 constitutes a cone-lock known from the prior art. However, this invention provides an extension of this cone-lock generally indicated at 30. The extension is provided with a urine outlet hole 31 communicating with the inner channel 29 through the cone-lock. This allows urine to be drained through the catheter when the catheter is in use. In the proximal end 21b, the inner catheter part 21 is provided with eyelets 32 for letting urine enter into the catheter.

The outer catheter part 22 is provided with a handle 33 at its distal end 22a. A urine collecting bag 5 may be attached to or attachable to the handle 33 so as to collect the urine. The handle 33 is provided with a sealing element 34 that cooperates with the extension 30 to prevent liquid from flowing through the catheter and out through the handle 33, when the catheter is stored.

When the catheter is stored (shown in FIG. 2), the inner catheter part is almost completely entered into the outer catheter part. The locking element 28 is positioned at the second stop 27, so that the outer catheter part 22 can move with respect to the inner catheter part 21. In this configuration of the catheter, any liquid (for example liquid swelling medium) entering into the catheter through the eyelets will be able to enter all the way through the inner catheter part 21, through the inner channel 29 through the cone-lock and out through the urine outlet hole 31 in the extension 30. However, the sealing element 34 will prevent it from flowing out through the distal end 33a of the handle and into a collecting bag (not shown) that is attached thereto.

When the catheter is to be used, it is removed from the package (indicated dashed at 40 in FIG. 2), and the catheter is extended to its fully extended position. In this configuration of the catheter, urine can flow into the catheter through the eyelets 32, through the inner catheter part 21, through the inner channel 29 of the cone-lock, through the outer catheter part 22 and out through the handle 33 to a collecting bag (not shown) attached thereto. This is because, in the extended position, the sealing element 34 is disengaged from the extension 30.

The invention claimed is:

1. A telescoping catheter comprising:
    an outer catheter portion having a proximal end and a distal end, the outer catheter portion including a handle and a sealing element extending in a radial direction from an inner surface of the handle;
    an inner catheter portion slidably received within the outer catheter portion such that the telescoping catheter can be transitioned from a stored configuration to a use configuration, the inner catheter portion having a proximal end and a distal end; and
    an extension element extending distally from a cone-lock formed on the inner catheter portion, the cone-lock including a conical surface formed between a first stop and a second stop with a lock portion located between the first stop and the second stop;
    wherein the extension element is adapted to cooperate with the sealing element to control the flow of liquid from the inner catheter portion out through the handle based on a position of the extension element relative to the sealing element.

2. The telescoping catheter of claim 1, wherein when the telescoping catheter is in the stored configuration the extension element contacts the sealing element to prevent liquid from flowing past the sealing element, and wherein when the telescoping catheter is in the use configuration the extension element is free from contact with the sealing element and liquid is free to flow past the sealing element.

3. The telescoping catheter of claim 2, wherein the telescoping catheter is transitioned from the stored configuration to the use configuration by sliding the inner catheter portion proximal relative to the outer catheter portion.

4. The telescoping catheter of claim 1, wherein the extension element includes an interior channel and an eyelet configured to allow fluid to pass through an interior of the extension element.

5. The telescoping catheter of claim 1, further including a collection bag coupled to the handle of the outer catheter portion.

6. The telescoping catheter of claim 5, wherein when the telescoping catheter is in the storage configuration the extension element contacts the sealing element to fluidly decouple the inner catheter portion from the collection bag, and wherein when the telescoping catheter is in the use configuration the extension element remains free from contact with the sealing element such that the inner catheter portion is fluidly coupled to the collection bag.

7. A telescoping catheter comprising:
    an outer catheter portion having a proximal end and a distal end, the outer catheter portion including a handle at the distal end and a sealing element formed on an inner surface of the handle;
    an inner catheter portion having a proximal end adapted for insertion into a bladder and a distal end, the inner catheter portion being slidably received by the outer catheter portion such that the telescoping catheter can be transitioned from a stored configuration to a use configuration;
    a cone-lock configured to fluidly couple the inner catheter portion to the outer catheter portion, the cone-lock including a conical surface formed between a first stop and a second stop, a locking portion located between the first stop and the second stop, and an extension element extending from the cone-lock distal the locking portion;
    wherein the locking portion moves relative to the conical surface such that the locking portion is engaged with and contacts an inner surface of the outer catheter portion in the use configuration and the locking portion is separated away from the inner surface of the outer catheter portion in the stored configuration;
    wherein the extension element is engaged with the sealing element of the handle to prevent the flow of liquid through the handle in the stored configuration; and
    a collection bag fluidly coupled to the handle.

8. The telescoping catheter of claim 7, wherein when the telescoping catheter is in the stored configuration the extension element contacts the sealing element to fluidly decouple the inner catheter portion from the collection bag, and wherein when the telescoping catheter is in the use configuration the extension element remains free from contact with the sealing element such that fluid is free to pass from the inner catheter portion to the collection bag.

9. The telescoping catheter of claim 8, wherein the telescoping catheter is transitioned from the stored configuration to the use configuration by sliding the inner catheter portion proximal relative to the outer catheter portion.

10. The telescoping catheter of claim 7, wherein the cone-lock includes an interior channel configured to allow fluid to pass through the cone-lock.

11. The telescoping catheter of claim 10, wherein the extension element includes an eyelet fluidly coupled to the interior channel of the cone-lock, the eyelet configured to allow fluid to pass through the extension element.

12. The telescoping catheter of claim 11, wherein when the telescoping catheter is in the storage configuration a portion of the cone-lock distal the eyelet contacts the sealing element to prevent fluid from flowing through the handle and into the collection bag.

13. A prepackaged catheter assembly comprising:
   a container forming a cavity containing a liquid and a cover attachable to the container;
   a telescoping catheter assembly sealed inside of the container, the telescoping catheter assembly including:
      an outer catheter portion having a sealing element proximate a distal end of the outer catheter portion;
      an inner catheter portion slidably received within the outer catheter portion, the inner catheter portion having an extension element extending distally away from a cone-lock, where the cone-lock includes a conical surface formed between a first stop and a second stop and a lock portion coupled to the conical surface; and
   wherein the liquid is in contact with the telescoping catheter assembly and the extension element is adapted to engage with the sealing element to prevent the liquid from exiting the cavity; and
   a collection bag stored in the cover, the collection bag coupled to the outer catheter portion.

14. The prepackaged catheter assembly of claim 13, wherein the outer catheter portion is slidably received by the inner catheter portion such that the telescoping catheter assembly can be selectively transitioned between a stored position and a use position.

15. The prepackaged catheter assembly of claim 14, wherein when positioned in the stored position, the contact between the extension element and the sealing element prevents liquid from exiting a distal end of the outer catheter portion.

16. The prepackaged catheter assembly of claim 13, wherein the telescoping catheter assembly further includes a handle coupled to the outer catheter portion.

17. The prepackaged catheter assembly of claim 16, wherein the collection bag is fluidly coupled to the handle.

18. The prepackaged catheter assembly of claim 14, wherein the cone-lock includes an interior channel configured to allow fluid to pass through the cone-lock.

19. The catheter assembly of claim 18, wherein the cone-lock includes an eyelet fluidly coupled to the interior channel of the cone-lock, the eyelet configured to allow fluid to pass through the extension element.

20. The catheter assembly of claim 19, wherein when the telescoping catheter assembly is in the stored configuration, a portion of the extension element distal the eyelet contacts the sealing element to prevent fluid from flowing into the collection bag.

21. The catheter assembly of claim 13, wherein the extension element is tapered.

22. The catheter assembly of claim 13, wherein the lock portion moves relative to the conical surface such that the lock portion is engaged with and contacts an inner surface of the outer catheter portion in the use configuration and the lock portion is separated away from the inner surface of the outer catheter portion in the stored configuration.

* * * * *